United States Patent [19]
Paciorek et al.

[11] Patent Number: 4,559,175
[45] Date of Patent: Dec. 17, 1985

[54] HALO-SUBSTITUTED DIPHOSPHA-S-TRIAZINES AND THEIR DERIVATIVES

[75] Inventors: Kazimiera J. L. Paciorek, Corona del Mar; Reinhold H. Kratzer, Irvine; David H. Harris, Sierra Madre; Mark E. Smythe, Pasadena; James H. Nakahara, Irvine, all of Calif.

[73] Assignee: The United States of America as represented by the Secretary of the Air Force, Washington, D.C.

[21] Appl. No.: 601,873

[22] Filed: Apr. 19, 1984

[51] Int. Cl.$^4$ .................... C07C 117/00; C07F 9/26
[52] U.S. Cl. .................... 260/349; 252/49.9; 252/389 A; 252/400 A; 260/543 PN; 260/927 N; 564/13; 568/12
[58] Field of Search ............ 260/349, 543 PN, 927 N; 568/12; 564/13

[56] References Cited

U.S. PATENT DOCUMENTS

| | | | |
|---|---|---|---|
| 2,649,464 | 8/1953 | Hartley et al. | 260/349 |
| 2,676,985 | 4/1954 | Husted | 260/465.7 X |
| 3,087,937 | 4/1963 | Tesi et al. | 260/349 |
| 3,183,251 | 5/1965 | Knowles et al. | 260/349 |
| 3,242,218 | 3/1966 | Miller | 562/586 X |
| 3,253,062 | 5/1966 | Reetz et al. | 260/543 PN X |
| 3,277,170 | 10/1966 | Paciorek et al. | 260/349 X |
| 3,562,298 | 2/1971 | Alexander et al. | 260/349 |
| 3,715,378 | 2/1973 | Sianesi et al. | 260/463 |
| 3,867,484 | 2/1975 | Beriger | 260/543 P X |
| 4,166,071 | 8/1979 | Paciorek et al. | 260/551 P |
| 4,215,072 | 7/1980 | Paciorek et al. | 260/551 P |
| 4,297,510 | 10/1981 | Paciorek et al. | 564/13 |

FOREIGN PATENT DOCUMENTS 1350806 4/1974 United Kingdom .

OTHER PUBLICATIONS

Chem. Abstracts, vol. 80, 70845e, p. 351 (1974).
Brown, J. Polym. Sci., 44, 9 (1960).
Fluck et al., Chem. Ber., 96, 3085 (1963).

*Primary Examiner*—Joseph Paul Brust
*Attorney, Agent, or Firm*—Donald J. Singer; William J. O'Brien

[57] ABSTRACT

This invention concerns itself with a novel class of dihalodiphospha-s-triazines as exemplified by the compound 1,3-bis[phenylchloro-phospha]-5-perfluoro-n-heptyl-2,4,6-triazines as well as their thio and azido substituted derivatives.

11 Claims, No Drawings

HALO-SUBSTITUTED DIPHOSPHA-S-TRIAZINES AND THEIR DERIVATIVES

STATEMENT OF GOVERNMENT INTEREST

The invention described herein may be manufactured and used by or for the Government for governmental purposes without the payment of any royalty thereon.

BACKGROUND OF THE INVENTION

This invention relates to novel halogen-substituted diphospha-s-triazines and to a method for their synthesis. In a more specific manner, this invention relates to a method for synthesizing halogen-substituted diphospha-s-triazines by effecting a reaction between an imidodiaryl-diphosphonic acid pentahalide and a perfluoroalkyl or perfluoroalkylether amidine, and to the novel diphospha-s-triazine compounds produced thereby.

The novel compounds of matter, namely the halo-substituted diphospha-s-triazines, are best represented by 1,3-bis(phenylchlorophospha)-5-perfluoroheptyl-2,4,6-triazine and 1,3-bis(phenylchlorophospha)-5-perfluoroalkylether-2,4,6-triazine, as well as their thio and azido derivatives such as 1,3-bis[phenyl(thiophenyl)-phospha]-5-perfluoroheptyl-2,4,6-triazine. The compounds of this invention and their thio and azido substituted triazine derivatives find application as antioxidant and anticorrosion additives for perfluorinated lubricating fluids and greases. Other applications requiring the use of antioxidant and anticorrosion agents will readily suggest themselves to those skilled in the art. The presence of sulfur in the thio-substituted materials also improves the lubricity of the resultant perfluorinated polyalkylether fluid formulations.

The present interest in the utilization of perfluoroalkylether type fluids for wide temperature range lubricating applications has created a need for effective antioxidant and anticorrosive additives in order to permit their functioning in the presence of metals and alloys at elevated temperatures. In the absence of additives in oxidizing atmospheres and in the presence of titanium alloys, the fluids as represented by Fomblin Z (a product of Montefluos, Italy; U.S. Pat. No. 3,715,378) and Krytox 143AC (a product of E. I. DuPont de Nemours and Company, Wilmington, Del., U.S. Pat. No. 3,242,218), undergo extensive degradation and metal corrosion at temperatures as low as 235° C. (455° F.).

In addition to their use as antioxidants, the halogenated diphospha-s-triazines of this invention can be substituted by a variety of groups and thus provide a series of novel compounds to be utilized as monomers in polymer formation.

SUMMARY OF THE INVENTION

The present invention resides in the synthesis of a novel class of diphospha-s-triazines having the following structural formula:

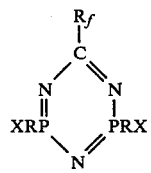

wherein X is a halogen selected from the group consisting of chlorine and bromine; $R_f$ is a perfluoroalkyl or perfluoroalkylether group, and R is an aryl group. Examples of the $R_f$ substituent include groups having the formula $C_nF_{2n+1}$, where n is an integer from 1 to 10, inclusive; $CF_3(OCF_2CF_2)_xOCF_2$, $C_2F_5-(OCF_2CF_2)_x-OCF_2$, and $C_3F_7[OCF(CF_3)CF_2]_xOCF(CF_3)$, where x is zero or an integer from 1 to 20, inclusive, preferably an integer from 1 to 4, inclusive. Examples of the R group include $C_6H_5$; $R'-C_6H_4$, where R' is an aromatic, alkyl, perfluoroalkyl or perfluoroalkylether moiety; and a perfluoroaryl, such as $C_6F_5$ and $R_f'-C_6F_4$, where $R_f'$ is a perfluoroalkyl or perfluoroalkylether group. The novel synthesis for preparing the halogen substituted diphospha-s-triazines of this invention comprises the interaction of a perfluorinated amidine with an imidodiaryl-diphosphinic acid pentahalide in the presence of an acid acceptor at temperatures from of from about 0° to 50° C. to yield the dihalodiphospha-s-triazines of this invention.

Accordingly, the primary object of this invention is to provide a series of novel dihalo-substituted diphospha-s-triazines.

Another object of this invention is to provide a novel method for synthesizing dihalo-substituted diphospha-s-triazines by effecting a reaction between a perfluorinated amidine and an imidodiaryl-diphosphonic acid pentahalide.

Still another object of this invention is to provide a series of dihalo-substituted diphospha-s-triazines that find particular utility as antioxidant and anticorrosive additives for perfluorinated lubricating fluids.

The above and still other objects and advantages of the present invention will become more readily apparent upon consideration of the following detailed disclosure thereof.

DESCRIPTION OF THE PREFERRED EMBODIMENTS

In accordance with this invention it has been found that the above-noted objects can be achieved by effecting a reaction between a solvent mixture of a perfluoralkyl or perfluoroalkylether amidine and an imidodiaryl-diphosphonic acid pentahalide. The reaction is carried out within an inert atmosphere, in the presence of an acid acceptor, and at temperatures and for periods of time sufficient to achieve the desired synthesis.

Previous diphospha-s-triazines, such as those disclosed in U.S. Pat. No. 4,215,072 to Paciorek et al, were substituted on the phosphorus ring atoms by aryl groups only and thus were not amenable to transformations into other types of compounds as is possible with the materials of the present invention. In the compounds of this invention, the halogen group X can be replaced by $N_3$, SR, or OR resulting in novel compositions. Examples of R include $C_6H_5$, $R'-C_6H_4$, where R' is an aromatic, alkyl, perfluoroalkyl or perfluoroalkylether moiety, and a perfluoroaryl, such as $C_6F_5$ and $R_f'-C_6F_4$, where $R_f'$ is a perfluoroalkyl or perfluoroalkylether group.

The procedure followed in synthesizing the dihalodiphospha-s-triazines of this invention can be represented by the following equation:

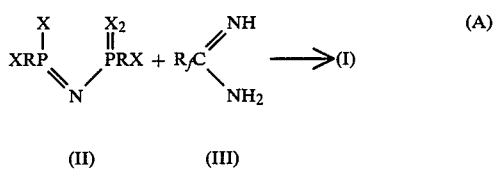

(II)   (III)

In the foregoing equation, $R_f$ and R are defined as above while X is chlorine or bromine. As shown by equation (A), the imidodiaryl-diphosphinic acid pentahalide (II) is reacted with a perfluoroalkyl or perfluoroalkylether amidine (III), giving the diphospha-s-triazine (I). The reaction is conducted in mixed solvents such as, e.g., tetrachloroethane and Freon-113 at temperatures ranging from about 0° C. to 50° C. in the presence of an acid acceptor, such as triethylamine, to promote hydrogen chloride elimination. The reaction is carried out for a period of time sufficient to effect the synthesis and usually ranges from 24–72 hours, although longer or shorter periods can be used. The reaction is carried out in an inert atmosphere, e.g., under nitrogen, helium, or argon. In general, equimolar amounts of reactants are used, although it is often preferred to employ an excess of the diphosphinic acid pentahalide.

The substitution of the halogen X in dihalophospha-s-triazine (III) by another group is carried out using either an alkali metal salt of the substituent or having an acid acceptor present. Thus, in the substitution of the halogen by the thio-group, a solution of the dihalodiphospha-s-triazine is reacted with thiophenol in a solvent such as tetrahydrofuran at temperatures ranging from about 0° to 50° C. in the presence of triethylamine. The product formed is the thiophenyl derivative (IV):

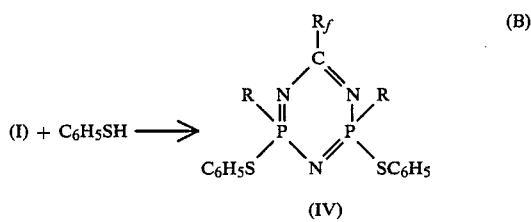

In a similar manner using lithium azide, the diazido triazine (IV) is formed from I:

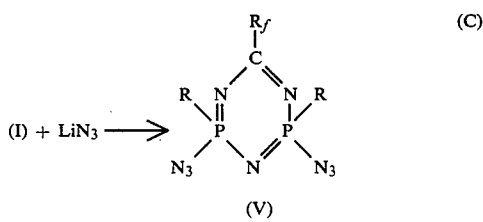

In equations (B) and (C) above, the $R_f$ substituent is defined as above in equation (A) and formula (I).

The materials that are used in preparing the triazine products are known compounds that are described in the literature. For example, imido-diphenyl-diphosphinic acid pentachloride is described by E. Fluck and R. M. Reinisch, Chem. Ber., 96, 3085 (1968). Perfluoro-n-heptylamidine is described by H. C. Brown in J. Polymer Sci., 44, 9 (1960) and by D. R. Husted in U.S. Pat. No. 2,676,985 (1954). Perfluoroalkylether amidines are described by P. D. Schuman et al in British Pat. No. 1,350,806 (1974).

A more complete understanding of the invention can be obtained by referring to the following illustrative examples which are not intended, however, to be unduly limitative of the invention.

EXAMPLE I

In an inert atmosphere enclosure to imido-diphenyl-diphosphinic acid pentachloride (14.83 g, 36.40 mmol) in tetrachloroethane (50 ml) was slowly added at room temperature a solution of perfluorooctanoyl-amidine (15.00 g, 36.40 mmol) and triethylamine (11.05 g, 109.2 mmol) in Freon-113 (120 ml). After stirring at room temperature for 71 hours, the precipitate (13.64 g of triethylamine hydrochloride) which was formed was filtered off. Subsequently, the solvents were removed in vacuo, initially at room temperature, then at 40° C. The residue was redissolved in Freon-113 and additional 0.70 g of triethylamine hydrochloride was filtered off bringing the total to 14.34 g (91.4%). The filtrate was then passed through a 1.5×3 cm column of neutral Woelm alumina and distilled giving 1,3-bis(phenyl-chlorophospha)-5-perfluoro-n-heptyl-2,4,6-triazine (20.53 g, 79.4% yield), bp 153–159/0.001 mm Hg; mp 59°–62° C.

Analysis calculated for $C_{20}H_{10}F_{15}N_3Cl_2P_2$: C, 33.83; H, 1.42; F, 40.13; N, 5.92; Cl, 9.99; P, 8.72; MW, 710.15. Found: C, 33.84; H, 1.66; F, 39.89; N, 5.93, Cl, 9.70; P, 8.74; MW, 747.

EXAMPLE II

In an inert atmosphere enclosure to imido-diphenyl-diphosphinic acid pentachloride (8.08 g, 19.80 mmol) in tetrachloroethane (40 ml) was slowly added at room temperature a solution of perfluoroalkylether amidine, $C_3F_7OCF(CF_3)CF_2OCF(CF_3)C(=NH)NH_2$ (9.80 g, 19.80 mmol), and triethylamine (6.02 g, 59.50 mmol) in Freon-113 (25 ml). After stirring at room temperature for 65 hours, a white precipitate (7.60 g, 93%) of triethylamine hydrochloride was isolated by filtration. Removal of solvents in vacuo, initially at room temperature, then at 50° C., gave a pale-yellow viscous liquid which was redissolved in Freon-113 and purified by filtration through a 1.5×4.0 cm column of neutral Woelm alumina. After solvent removal, distillation gave 1,3-bis(phenylchlorophospha)-5-[$C_3F_7OCF(CF_3)CF_2OCF(CF_3)$]-2,4,6-triazine (9.41 g, 60% yield) bp 114°–121° C./0.001 mm Hg.

Analysis calculated for $C_{21}H_{10}F_{17}Cl_2N_3O_2P_2$: C, 31.84; H, 1.27; F, 40.77; Cl, 8.95; N, 5.30; O, 4.04; P, 7.82; MW, 792.16. Found: C, 31.90; H, 1.51; F, 41.06; Cl, 8.72; N, 5.21, P, 7.83; MW, 810.

EXAMPLE III

In an inert atmosphere enclosure to a stirred solution of 1,3-bis(phenylchlorophospha)-5-perfluoro-n-heptyl-2,4,6-triazine (2.00 g, 2.82 mmol) in tetrahydrofuran (10 ml) at room temperature was added a solution of thiophenol (0.62 g, 5.64 mmol) and triethylamine (0.57 g, 5.64 mmol) in tetrahydrofuran (15 ml) over a period of 30 minutes. An immediate reaction was observed with formation of white precipitate. After stirring at room temperature for 20 hours, the reaction mixture was filtered giving triethylamine hydrochloride 90.68 g, 88% yield) and a pale yellow filtrate. Removal of solvents in vacuo from the filtrate gave a pale yellow liquid which was redissolved in Freon-113 and passed through a 1.0×4.0 cm column of neutral Woelm alumina. The solid, which crystallized on standing after solvent removal, was recrystallized from hot hexane to give 1,3-bis[phenyl(thiophenyl)phospha]-5-perfluoro-n-heptyl-2,4,6-triazine (1.72 g, 71% yield), mp 89° to 91° C.

Analysis calculated for $C_{32}H_{20}F_{15}N_3S_2P_2$: C, 44.82; H, 2.35; F, 33.23; N, 4.90; S, 7.48; P, 7.22; MW, 857.58. Found: C, 44.70; H, 2.37; F, 33.98; N, 4.96; S, 7.68; P, 7.21; MW, 881.

EXAMPLE IV

In an inert atmosphere enclosure to a stirred solution of thiophenol (1.39 g, 12.62 mmol) and triethylamine (1.05 g, 10.38 mmol) in tetrahydrofuran (10 ml) at room temperature was added a solution of 1,3-bis(phenylchlorophospha)-5-[$C_3F_7OCF(CF_3)CF_2OCF(CF_3)$]-2,4,6-triazine (4.11 g, 5.19 mmol) in tetrahydrofuran (15 ml) over a period of 50 minutes. An immediate reaction was observed with formation of a white precipitate. The flask was covered with aluminum foil (to prevent diphenyldisulfide formation and the reaction mixture was left to stir at room temperature for 19 hours. Filtration gave triethylamine hydrochloride (1.36 g, 95%) and a pale yellow filtrate. The residue left after solvent evaporation was redissolved in a minimum of Freon-113 and passed through a 0.8×7.0 cm column of neutral Woelm alumina. Removal of Freon-113 in vacuo gave 1,3-bis[phenyl(thiophenyl)phospha]-5-[$C_3F_7OCF(CF_3)CF_2OCF(CF_3)$]-2,4,6-triazine as a pale yellow viscous liquid (4.50 g, 92% yield), bp 189° C./0.001 mm Hg.

Analysis calculated for $C_{33}H_{20}F_{17}N_3O_2S_2P_2$: C, 42.18, H, 2.15; F, 34.37; N, 4.47; P, 6.60; MW, 939.59. Found: C, 42.35; H, 2.33; F, 34.65; N, 4.47; P, 6.17; MW, 950.

EXAMPLE V

In an inert atmosphere enclosure to a slurry of lithium azide (1.00 g, 20.43 mmol) in acetonitrile (10 ml) was added a solution of 1,3-bis(phenylchlorophospha)-5-perfluoro-n-heptyl-2,4,6-triazine (5.00 g, 7.04 mmol) in acetonitrile (40 ml). After stirring at room temperature for 40 hours, the reaction mixture was filtered to afford a white precipitate of lithium chloride and excess lithium azide, and a pale yellow filtrate which gave a moderately viscous yellow liquid on removal of solvents in vacuo. The oil was redissolved in Freon-113 and was passed through a 1.0×5.0 cm column of neutral Woelm alumina. Distillation gave 1,3-bis(azidophenylphospha)-5-perfluoro-n-heptyl-2,4,6-triazine as a colorless liquid (3.61 g, 71% yield), bp 148° to 150° C./0.001 mm Hg.

Analysis calculated for $C_{20}H_{10}F_{15}N_9P_2$: C, 33.21; H, 1.39; F, 39.40; N, 17.43; P, 8.56; NW, 723.28. Found: C, 33.32; H, 1.61; F, 40.07; N, 17.02; P, 8.56; MW, 760.

EXAMPLE VI

In an inert atmosphere enclosure to a solution of 1,3-bis(azidophenylphospha)-5-perfluoro-N-heptyl-2,4,6-triazine (1.25 g, 1.73 mmol) in benzene (10 ml) was aded a solution of freshly sublimed triphenylphosphine (1.10 g, 4.19 mmol) in benzene (5 ml). After stirring at room temperature for 20 hours, the mixture was heated at reflux temperature under nitrogen by-pass for 45 hours. Solvents were removed in vacuo at room temperature; this was followed by heating at 70° to 90° C. for 10 hours to remove, by sublimation, the excess triphenylphosphine. The solid product was redissolved in a minimum of Freon-113 and passed through a 1.0×4.0 cm column of neutral Woelm alumina. Removal of volatiles in vacuo afforded 1,3-bis[phenyl(triphenylphosphine-iminophospha)]-5-perfluoro-n-heptyl-2,4,6-triazine (1.46 g, 71% yield) as a white solid, mp 59° to 65° C.

Analysis calculated for $C_{56}H_{40}F_{15}N_5P_4$: C, 56.44; H, 3.38; F, 23.91; N, 5.88; P, 10.40; MW, 1191.84. Found: C, 56.57; H, 3.61; F, 22.83; N, 5.72; P, 9.74; MW, 1210.

The antioxidative and anticorrosive action of 1,3-bis[phenyl(thiophenylphospha)]-5-[$C_3F_7OCF(CF_3)CF_2OCF(CF_3)$]2,4,6-triazine on different types of perfluoroalkylether fluids is illustrated by a series of tests carried out at elevated temperatures in oxygen in the presence of Ti(4Al, 4Mn) alloy using Krytox 143AC fluid, a product of E. I. Dupont de Nemours and Company, Wilmington, Del., and Fomblin Z fluid, a product of Montefluos of Italy. Control runs in the absence of the additive were conducted under otherwise identical conditions. In a test, a coupon of Ti(4Al, 4Mn) alloy is suspended in a sealed tube containing either a fluid alone or fluid plus the additive. The exposure duration and temperatures are listed in the table below. The action of the additives is clearly evident from the drastically reduced amount of volatiles formed, oxygen consumed, and the unchanged appearance of the metal coupon.

TABLE I

| Fluid type | Amt g | Additive wt % | Temp °C. | Exposure hr | Oxygen consumed | | Total Product formed | |
|---|---|---|---|---|---|---|---|---|
| | | | | | mg | mg/g[1] | mg | mg/g[2] |
| Krytox 143AC | 4.79 | none | 316 | 24 | 75 | 15.7 | 758.7 | 158.4 |
| Krytox 143AC | 4.89 | 1% | 316 | 24 | 2 | 0.4 | 8.5 | 1.7 |
| Fomblin Z | 3.67 | none | 288 | 8 | 47 | 12.7 | 2228.7 | 607.3 |
| Fomblin Z | 6.2 | 2% | 288 | 8 | 3 | 0.4 | 8.4 | 1.2 |

[1]Oxygen consumed in mg/g fluid employed.
[2]Products formed in mg/g fluid employed.

While the invention has been described with particularity in reference to specific embodiments thereof, it is to be understood that the disclosure thereof is for the purpose of illustration only and is not to be considered as limiting the invention in any way, the scope of which is defined by the appended claims.

What is claimed is:

1. The compound 1,3-bis[phenylchlorophospha]-5-perfluoro-n-heptyl-2,4,6-triazine.

2. A process for synthesizing 1,3-bis(phenylchlorophospha)-5-perfluoro-n-heptyl-2,4,6-triazine which comprises the steps of:

(a) forming a reaction mixture consisting essentially of (1) a solution of perfluorooctanoylamidine and triethylamine and (2) imido-diphenyl-diphosphinic acid pentachloride;

(b) heating and stirring said reaction mixture at room temperature for a period of time of about 71 hours and
(c) separating the resultant reaction product.

3. The compound 1,3-bis[phenylchlorophospha]-5-[C$_3$F$_7$OCF(CF$_3$)CF$_2$OCF(CF$_3$)]-2,4,6-triazine.

4. A process for synthesizing 1,3-bis(phenylchlorophospha)-5-[C$_3$F$_7$OCF(CF$_3$)CF$_2$OCF(CF$_3$)]-2,4,6-triazine which comprises the steps of:
 (a) forming a reaction mixture by slowly adding a first solution consisting essentially of a perfluoroalkylether amidine having the structural formula C$_3$F$_7$OCF(CF$_3$)CF$_2$OCF(CF$_3$)C(=NH)NH$_2$ and triethylamine to a second solution composed of imido-diphenyl-diphosphonic acid pentachloride and tetrachloroethane;
 (b) stirring said reaction mixture at about room temperature for about 65 hours; and
 (c) separating the resulting reaction product.

5. The compound 1,3-bis[phenyl(thiophenyl)phospha]-5-perfluoro-n-heptyl-2,4,6-triazine.

6. A process for synthesizing 1,3-bis[phenyl(thiophenyl)phospha]-5-perfluoro-n-heptyl 2,4,6-triazine which comprises the steps of:
 (a) forming a reaction mixture by adding a first solution consisting essentially of thiophenol, triethylamine and tetrahydrofuran to a second solution consisting essentially of 1,3-bis(phenylchlorophospha)-5-perfluoro-n-heptyl 2,4,6-triazine and tetrahydrofuran;
 (b) stirring said reaction mixture at about room temperature for about 20 hours; and
 (c) separating the resultant reaction product.

7. The compound 1,3-bis[phenyl(thiophenyl)phospha]-5-[C$_3$F$_7$OCF(CF$_3$)CF$_2$OCF(CF$_3$)]-2,4,6-triazine.

8. A process for synthesizing 1,3-bis[phenyl(thiophenyl)phospha]-5-[C$_3$F$_7$OCF(CF$_3$)CF$_2$OCF(CF$_3$)]-2,4,6-triazine which comprises the steps of:
 (a) forming a reaction mixture by slowly adding first solution consisting essentially of 1,3-bis(phenylchlorophospha)-5-[C$_3$F$_7$OCF(CF$_3$)CF$_2$OCF(CF$_3$)]-2,4,6-triazine and tetrahydrofuran to a second solution consisting essentially of thiophenol, triethylamine and tetrahydrofuran;
 (b) stirring said reaction mixture at room temperature for about 19 hours; and
 (c) separating the resultant reaction product.

9. The compound 1,3-bis(azidophenylphospha)-5-perfluoro-n-heptyl-2,4,6-triazine.

10. A process for synthesizing 1,3-bis(azidophenylphospha)-5-perfluoro-n-heptyl-2,4,6-triazine which comprises the steps of:
 (a) forming a reaction mixture by adding a solution consisting essentially of 1,3-bis(phenylchlorophospha)-5-perfluoro-n-heptyl-2,4,6-triazine and acetonitrile to a slurry consisting essentially of lithium azide and acetonitrile;
 (b) stirring said reaction mixture at room temperature for about 40 hours; and
 (c) separating the resultant reaction product.

11. The compound 1,3-bis[phenyl(triphenyl-phosphineiminophospha)]-5-perfluoro-n-heptyl-2,4,6-triazine.

* * * * *